(12) United States Patent
Baek et al.

(10) Patent No.: US 11,213,260 B2
(45) Date of Patent: Jan. 4, 2022

(54) METHOD AND APPARATUS FOR CORRECTING CONE-BEAM ARTIFACT IN CONE-BEAM COMPUTED TOMOGRAPHY IMAGE, AND CONE-BEAM COMPUTED TOMOGRAPHY APPARATUS INCLUDING THE SAME

(71) Applicant: Industry-Academic Cooperation Foundation, Yonsei University, Seoul (KR)

(72) Inventors: Jongduk Baek, Incheon (KR); Chulhee Han, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 142 days.

(21) Appl. No.: 16/852,837

(22) Filed: Apr. 20, 2020

(65) Prior Publication Data
US 2020/0330057 A1 Oct. 22, 2020

(30) Foreign Application Priority Data
Apr. 19, 2019 (KR) .................. 10-2019-0046355

(51) Int. Cl.
*A61B 6/00* (2006.01)
*A61B 6/03* (2006.01)

(52) U.S. Cl.
CPC ............ *A61B 6/4085* (2013.01); *A61B 6/032* (2013.01); *A61B 6/467* (2013.01)

(58) Field of Classification Search
CPC ....... A61B 6/032; A61B 6/4085; A61B 6/467; A61B 6/03; A61B 6/4208; A61B 6/5258;
(Continued)

(56) References Cited

U.S. PATENT DOCUMENTS

2011/0081071 A1* 4/2011 Benson ................. G06T 11/005
382/154
2014/0328450 A1* 11/2014 Pal ....................... G01N 23/046
378/5
(Continued)

FOREIGN PATENT DOCUMENTS

JP 2015-117772 A 6/2015

*Primary Examiner* — Irakli Kiknadze
(74) *Attorney, Agent, or Firm* — Paratus Law Group, PLLC

(57) ABSTRACT

Disclosed is a technique for quickly removing and correcting a cone-beam artifact generated in a computed tomography (CT) image in consideration of bone and soft tissue regions when using a large-area X-ray detector in order to reduce a CT imaging time for large volumes in a cone-beam CT system. An apparatus includes an input unit configured to receive a start image including a cone-beam artifact, a computation unit configured to separate a high-density material image and a low-density material image from the start image received by the input unit, generate a reproduced image in which the cone-beam artifact is reproduced using the low-density material image, execute a correction process for subtracting the reproduced image from the start image to generate a corrected image, and iterate the correction process using the corrected image as a start image; and an output unit configured to output a final corrected image generated.

25 Claims, 14 Drawing Sheets

(58) Field of Classification Search
CPC ....... A61B 6/583; A61B 6/482; A61B 6/5205;
A61B 6/582; A61B 6/488; A61B 6/545;
G06T 2207/10072; G06T 2207/10116;
G06T 2207/30012; G06T 5/002; G06T
11/005; G06T 2207/10081; G06T
2207/20182; G06T 11/008; G01N
2223/401; G01N 2223/419; G01N
23/046; G01N 2223/618; G01N 33/025;
G01V 5/005; H05B 2206/046; H05B
6/6408; H05B 6/6494; H05B 6/6497;
H05B 6/782
USPC .......................................... 378/4, 19, 62, 901
See application file for complete search history.

(56) References Cited

U.S. PATENT DOCUMENTS

| | | | |
|---|---|---|---|
| 2015/0170341 A1* | 6/2015 | Fan ...................... | A61B 6/5205 |
| | | | 378/4 |
| 2020/0060793 A1* | 2/2020 | Boyle .................. | A61C 9/0046 |

* cited by examiner (a)

(b)

(a)

(b)

METHOD AND APPARATUS FOR CORRECTING CONE-BEAM ARTIFACT IN CONE-BEAM COMPUTED TOMOGRAPHY IMAGE, AND CONE-BEAM COMPUTED TOMOGRAPHY APPARATUS INCLUDING THE SAME

CROSS-REFERENCE TO RELATED APPLICATION

This application claims priority to Korean Patent Application No. 10-2019-0046355 (filed on Apr. 19, 2019), which is hereby incorporated by reference in its entirety.

BACKGROUND

The present invention relates to a method and apparatus for correcting a cone-beam artifact in a cone-beam computed tomography image and a cone-beam computed tomography apparatus including the same, and more particularly, to a correction method for quickly removing a cone-beam artifact generated in a computed tomography (CT) image in consideration of bone and soft tissue regions when using a large-area X-ray detector in order to reduce a CT imaging time for large volumes in a cone-beam CT system.

Technological advances in flat-panel detectors have made it possible to image a large volume range with a single gantry rotation of a cone-beam computed tomography (CBCT) system. A large two-dimensional (2D) detector array used in a CBCT system provides high-resolution images having a viewing angle of 30×30×30 cm$^3$ or more. Therefore, a CBCT system is widely used in various image diagnosis processes such as image-guided radiation therapy, a thoracic endometriosis image, root canal imaging, and a head measurement analysis.

A CBCT system provides information that is regarding a good shape f a patient and that has three-dimensional (3D) volumetric data, but a method of acquiring data in a circular-orbital cone-beam shape does not provide sampling sufficient for accurate reconstruction. An image reconstructed using a Feldkamp, Davis and Kress (FDK) algorithm, which is currently used, includes cone-beam artifacts that become more severe as the cone angle increases. Since such cone-beam artifacts interfere with diagnosis, an appropriate correction method is required.

Several algorithms have been proposed to reduce cone-beam artifacts. Grass proposed a modified FDK algorithm that uses a data relocation process to rearrange cone-beams in parallel (P-FDK) and tent (T-FDK) shapes to increase object sampling density. Chen proposed a weighted filtered back-projection algorithm in which each light ray is multiplexed by the inverse of the cosine function before back-projection in order to compensate for the strength degradation of the FDK algorithm. MaaB proposed an iterative approach for estimating cone-beam artifacts and then reducing cone-beam artifacts extracted from a FDK image. A modified FDK image was used to estimate a cone-beam artifact image subtracted from an original FDK image, and the cone-beam artifacts were reduced by iterating this procedure. This approach is effective in reducing cone-beam artifacts. However, since it requires more than 400 iterations, the approach needs an excessive amount of time to process images and thus has not been applied to practical clinical applications.

A two-pass algorithm proposed by Hsieh reduced a computation time because cone-beam artifacts are reduced in one iteration. A high-density material is treated as a dominant factor to generate cone-beam artifacts in FDK images. Accordingly, first, the high-density material is separated, and cone-beam artifacts are reproduced from the separated high-density material. Then, the reproduced image is subtracted from the original FDK image. The two-pass algorithm is very effective at a cone angle of less than 5°, but has a problem in which correction performance is degraded at a greater angle or in a region where bone density is not high.

RELATED ART DOCUMENTS

Patent Documents

Japanese Patent Publication No. 2015-117772 (published on Aug. 13, 2015)

SUMMARY

The present invention is proposed to solve the above-mentioned problems and is directed to providing a technique associated with a correction method for quickly removing a cone-beam artifact generated in a computed tomography (CT) image in consideration of bone and soft tissue regions when using a large-area X-ray detector in order to reduce a CT imaging time for large volumes in a cone-beam CT system.

According to an aspect of the present invention, there is provided an apparatus for correcting a cone-beam artifact in a cone-beam computed tomography image, the apparatus including an input unit configured to receive a start image including a cone-beam artifact; a computation unit configured to separate a high-density material image and a low-density material image from the start image received by the input unit, generate a reproduced image in which the cone-beam artifact is reproduced using the low-density material image, execute a correction process for subtracting the reproduced image from the start image to generate a corrected image, and iterate the correction process using the corrected image as a start image; and an output unit configured to output a final corrected image generated by the computation unit.

Also, the correction process of the computation unit may be iterated until a mean squared error (MSE) of the reproduced image satisfies a preset convergence criterion.

Also, the number of iterations of the correction process of the computation unit may be five or less.

Also, the computation unit may include a separation unit configured to separate the high-density material image and the low-density material image from the start image; a scalar calculation unit configured to compute an averaged scalar value using the low-density material image generated by the separation unit; a scalar removal unit configured to subtract the scalar value computed by the scalar calculation unit from the high-density material image generated by the separation unit to generate a high-density conversion object; a reproduction unit configured to generate a high-density conversion image using the high-density conversion object generated by the scalar removal unit and generate a reproduced image by subtracting the high-density conversion image from the high-density conversion object; and a correction unit configured to generate a corrected image by subtracting the reproduced image from the start image.

Also, the separation unit may use a thresholding method to separate the start image into the high-density material image and the low-density material image.

Also, the separation unit may compute an average of voxels corresponding to 90% or more of the maximum voxel in a high-density material region and may set a value corresponding to 55% to 75% of the average of the voxel as an initial threshold value for the thresholding method.

Also, the separation unit may increase the threshold value for the thresholding method each time the correction process is iterated.

Also, the threshold value may be linearly increased each time the correction process is iterated.

Also, the threshold value may be increased by 2.5% to 5%.

Also, the threshold value is no longer increased to prevent oversegmentation when the number of iterations of the correction process exceeds three.

Also, the separation unit may apply a median filter to the separated high-density material image.

Also, the scalar calculation unit may calculate the scalar value $\mu_{\tau(1)}$ using the following equation:

$$\mu_{\tau(1)} = \frac{1}{N}\sum_{n=1}^{N} f_{tissue,\tau(1)}(n)$$

where $f_{tissue,\tau(1)}$ is a low-density material image, N is the number of low-density material elements, and i is an operating order of the correction process.

Also, the reproduction unit may generate the high-density conversion image using a forward projection method and a Feldkamp, Davis and Kress (FDK) algorithm.

According to another aspect of the present invention, there is provided a method of correcting a cone-beam artifact in a cone-beam computed tomography image, the method including: causing an input unit to receive a start image including a cone-beam artifact; causing a separation unit to separate a high-density material image and a low-density material image from the start image; causing a scalar calculation unit to compute an averaged scalar value using the low-density material image generated by the separation unit; causing a scalar removal unit to subtract the scalar value computed by the scalar calculation unit from the high-density material image generated by the separation unit to generate a high-density conversion object; causing a reproduction unit to generate a high-density conversion image using the high-density conversion object generated by the scalar removal unit; causing the reproduction unit to generate a reproduced image by subtracting the high-density conversion image from the high-density material image generated by the separation unit; causing a correction unit to generate a corrected image by subtracting the reproduced image from the start image; and causing an output unit to output a final corrected image.

Also, the method may further include, after the causing of the correction unit to generate the corrected image by subtracting the reproduced image from the start image, causing the correction unit to compute a mean-squared error (MSE) of the reproduced image and check whether the MSE satisfies a preset convergence criterion and causing the correction unit to apply the corrected image as a start image when the MSE does not satisfy the preset convergence criterion, wherein a process from the causing of the separation unit to separate the high-density material image and the low-density material image from the start image to the causing of the correction unit to generate a corrected image by subtracting the reproduced image from the start image is iterated until an MSE of the corrected image satisfies a preset criterion.

Also, the causing of the separation unit to separate the high-density material image and the low-density material image from the start image may include separating the start image into the high-density material image and the low-density material image using a thresholding method.

Also, the causing of the separation unit to separate the high-density material image and the low-density material image from the start image may include computing an average of voxels corresponding to 90% or more of the maximum voxel in a high-density material region and setting a value corresponding to 55% to 75% of the average of the voxel as an initial threshold value for the thresholding method.

Also, the causing of the separation unit to separate the high-density material image and the low-density material image from the start image may include increasing the threshold value for the thresholding method each time the generation of the corrected image is iterated.

Also, the causing of the separation unit to separate the high-density material image and the low-density material image from the start image may include increasing the threshold value linearly.

Also, the causing of the separation unit to separate the high-density material image and the low-density material image from the start image may include increasing the threshold value by 2.5% to 5%.

The causing of the separation unit to separate the high-density material image and the low-density material image from the start image may include no longer increasing the threshold value in order to prevent oversegmentation when the number of generations of the corrected image exceeds three.

The method may further include, after the causing of the separation unit to separate the high-density material image and the low-density material image from the start image, causing the separation unit to apply a median filter to the separated high-density material image.

Also, the causing of the scalar calculation unit to compute the averaged scalar value using the low-density material image generated by the separation unit may include calculating the scalar value $\mu_{\tau(1)}$ using the following equation:

$$\mu_{\tau(1)} = \frac{1}{N}\sum_{n=1}^{N} f_{tissue,\tau(1)}(n)$$

where $f_{tissue,\tau(1)}$ is a low-density material image, N is the number of low-density material elements, and i is an operating order of the correction process.

Also, the causing of the reproduction unit to generate the high-density conversion image using the high-density conversion object generated by the scalar removal unit may include generating the high-density conversion image using a forward projection method and a Feldkamp, Davis and Kress (FDK) algorithm.

According to the method and apparatus for correcting a cone-beam artifact in a cone-beam computed tomography image and a cone-beam computed tomography apparatus including the same, it is possible to obtain the following advantageous effects.

First, the present invention can be applied immediately to CT systems currently being used compared to the conventional proposed technique and thus is easy to disseminate and the CT systems can be effectively improved.

Second, the present invention is excellent in cone-beam artifact correction performance and has high computation speed compared to the conventional cone-beam artifact correction technique. Therefore, the present invention is applicable to even a large-area X-ray detector that generates a large cone angle.

Third, the present invention accurately estimates a high-density material, which is a main cause of generating cone-beam artifacts, using a median filter, and also considers computation for low-density materials, and thus has better correction performance even in an environment where several materials are mixed than the conventional technique.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION

Figure 1:
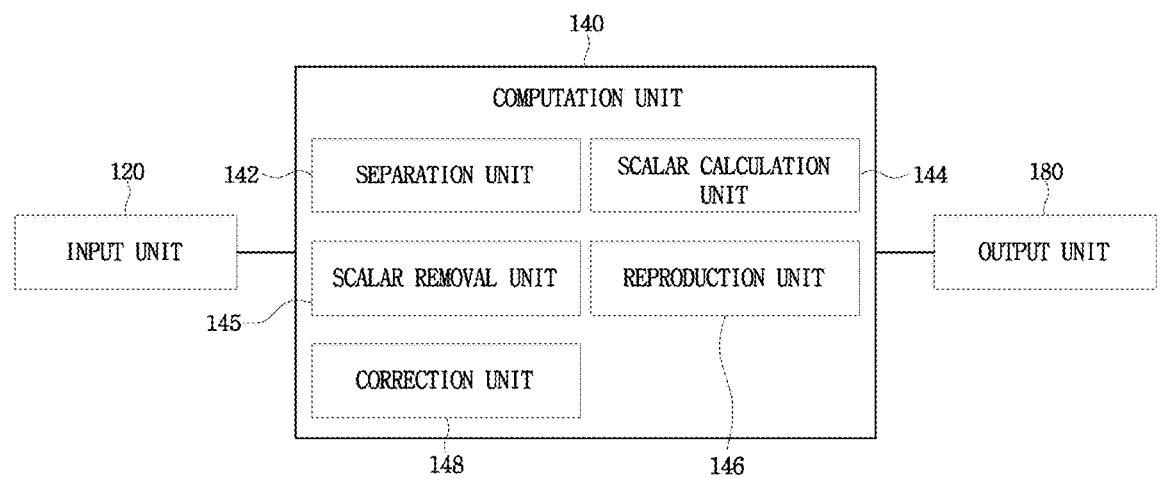
FIG. 1 is a block diagram showing a configuration of an apparatus for correcting a cone-beam artifact in a cone-beam computed tomography (CT) image according to an embodiment of the present invention.

Hereinafter, a method and apparatus for correcting a cone-beam artifact in a cone-beam computed tomography image and a cone-beam computed tomography apparatus including the same according to embodiments of the present invention will be described in detail with reference to the accompanying drawings. While the invention is susceptible to various modifications and alternative forms, specific embodiments thereof will be described in detail and shown by way of example. However, it is to be understood that the present invention is not limited to the specific exemplary embodiments but includes all modifications, equivalents, and substitutions within the spirit and scope of the present invention. In describing each drawing, like reference numerals are to be used for like elements.

Unless otherwise defined, all terms (including technical and scientific terms) used herein have the same meaning as commonly understood by those skilled in the art. It is to be understood that the terms defined by the dictionary are identical with the meanings within the context of the related art, and they should not be ideally or excessively formally defined unless the context clearly dictates otherwise.

The method and apparatus for correcting a cone-beam artifact in a cone-beam computed tomography image and the cone-beam computed tomography apparatus including the same according to embodiments of the present invention may be carried out through installation and operation in a single computer apparatus or through distributed installation and cooperation using a network configured by each computer in a wired or wireless manner.

Referring to FIG. 1, a correction apparatus according to an embodiment includes an input unit 120 configured to receive a start image including a cone-beam artifact and a 140 configured to separate a high-density material image and a low-density material image from the start image received by the input unit 120, generate a reproduced image in which the cone-beam artifact is reproduced using the low-density material image, execute a correction process for subtracting the reproduced image from the start image to generate a corrected image, and iterate the correction process using the corrected image as a start image. Also, the correction apparatus includes an output unit 180 configured to output a final corrected image generated by the computation unit 140.

The start image received by the input unit 120 is a Feldkamp, Davis and Kress (FDK) image captured by a cone-beam computed tomography (CBCT) apparatus.

A high-density material indicates a region determined as a bone, and a low-density material indicates a region determined as a soft tissue other than bone.

Since a cone-beam artifact is generated in both of a high-density material (bone) and a low-density material (a soft tissue), a cone-beam artifact caused by the low-density material is removed according to this embodiment unlike a conventional technique.

By considering correction of a cone-beam artifact generated in a soft tissue in this embodiment, it is possible to obtain a corrected image in which most cone-beam artifacts are removed even in an environment where a cone angle is greater than or equal to 10 degrees.

The first start image received by the input unit 120 is an image captured by a cone-beam computed tomography (CBCT) system.

The computation unit 140 includes a separation unit 142 configured to separate a high-density image and a low-density image from the start image received by the input unit 120, a scalar calculation unit 144 configured to compute an averaged scalar value using the low-density material image generated by the separation unit 142, a scalar removal unit 145 configured to subtract the scalar value computed by the scalar calculation unit 144 from the high-density material image generated by the separation unit 142 to generate a high-density conversion object, a reproduction unit 146 configured to generate a high-density conversion image using the high-density conversion object generated by the scalar removal unit 145 and generate a reproduced image by subtracting the high-density conversion image from the high-density conversion object, and a correction unit 148 configured to generate a corrected image by subtracting the reproduced image from the start image.

The separation unit 142 uses a thresholding method to separate the start image into the high-density material image and the low-density material image. In the thresholding method, based on a set threshold value, information greater than or equal to the threshold value and information less than the threshold value are separated from each other.

The separation unit 142 according to this embodiment computes the average of voxels corresponding to 90% or more of the maximum voxel of the high-density material region and sets a value corresponding to 55% to 75% of the average of the voxel as the first threshold value for the thresholding method.

Figure 2:
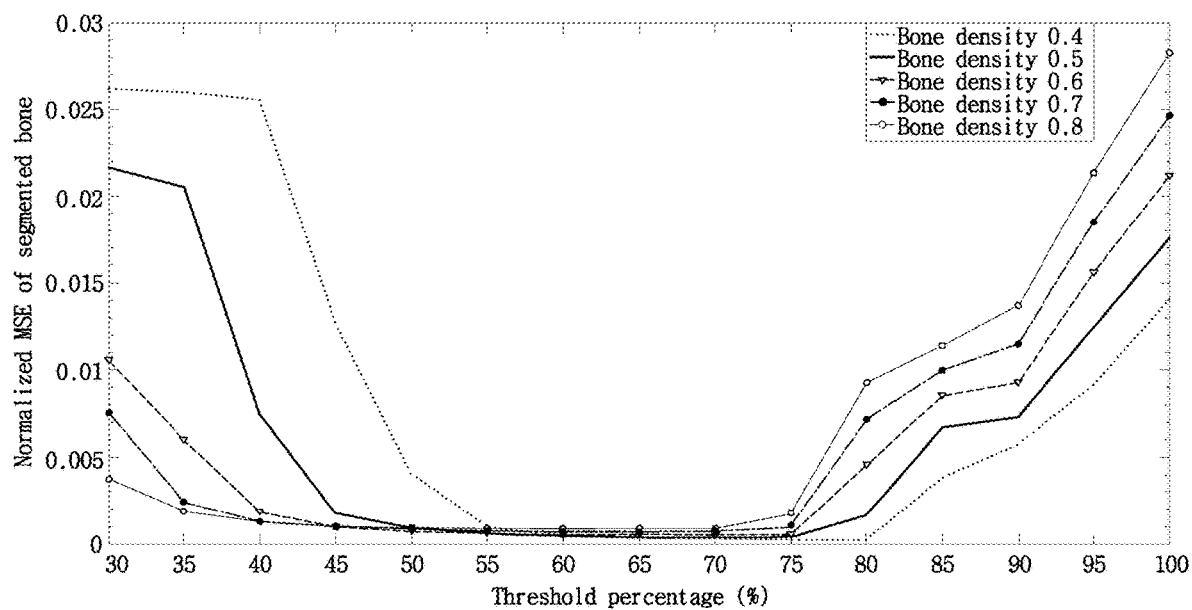
FIG. 2 is a graph obtained by computing a normalized means-squared error (NMSE) for five phantoms having different bone densities using a function of threshold percentage.

FIG. 2 is a graph obtained by computing a normalized means-squared error (NMSE) for five phantoms having different bone densities using a function of threshold percentage. In order to investigate the effect of the threshold value when the threshold value was not suitable, the NMSE was computed using an image with a cone-beam artifact. As a result of the experiment, it was confirmed that bones having a medium density of $0.4 \times 120$ cm$^{-1}$ had the smallest NMSE in a threshold value range of 55% to 75%. Therefore, a value corresponding to 65%, which is a medium value, may be set as the first threshold value.

Also, the separation unit 142 increases the threshold value of the thresholding method every time the correction process is iterated.

The threshold value is linearly increased every time the correction process is iterated.

A result of the experiment showed that performance is favorable when the threshold value is increased by 2.5% to 5%. When the correction process is iterated, a bone density increases, and thus a small NMSE region increases. Therefore, when the correction process is iterated, a larger tolerance is provided upon setting of the threshold value.

In particular, when the number of iterations of the correction process exceeds three, the threshold value is no longer increased to prevent oversegmentation.

The separation unit 142 applies a median filter to the separated high-density material image. The median filter, which is a filter that uses a median, functions to smooth a noise region generated in the image and to compute and remove outliers. The median filter may reduce a segmentation error caused by cone-beam artifacts and noise while a high-density material is separated using thresholding.

Figure 3:
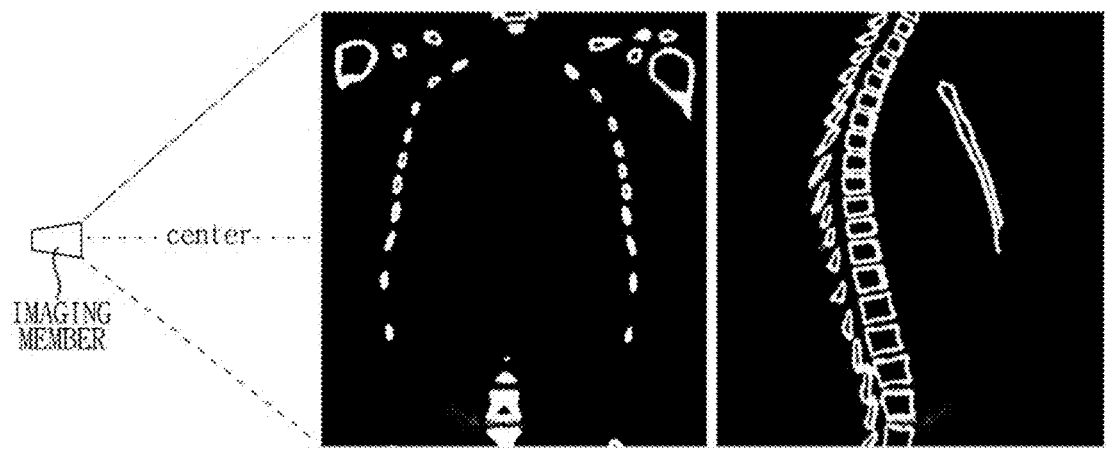
FIG. 3 is a diagram showing a high-density material image separated by a separation unit in a thresholding method.
Figure 4:
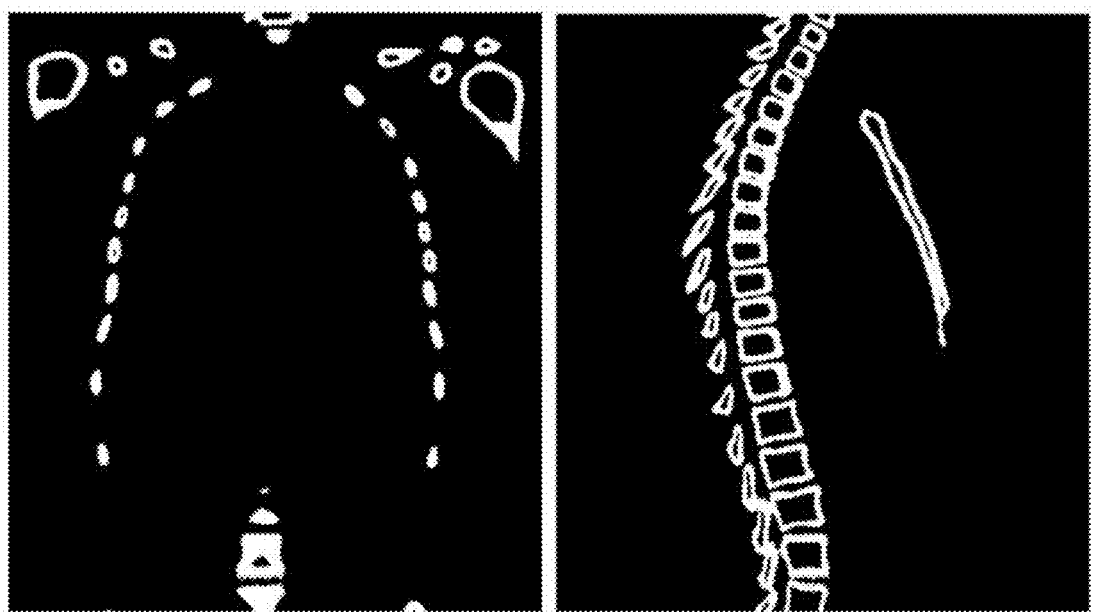
FIG. 4 is a diagram showing an image obtained by applying a median filter to the image shown in FIG. 3.

An imaging member of a cone-beam computed tomography (CBCT) apparatus is usually placed on the center of an image to be captured. As the imaging angle of the imaging member increases in the z-direction, that is, the imaging member moves to an edge of an imaging range, the amount of generated distortion increases compared to a region opposite to the imaging member. FIG. 3 shows a high-density material image separated by a separation unit 142 in a thresholding method. Referring to FIG. 3, it can be seen that a segmentation error in which a plurality of white dots are densely formed between spinal bones has occurred due to distortion at the bottom of the high-density material image (as indicated by a red arrow). FIG. 4 shows an image obtained by applying a median filter to the image shown in FIG. 3. Referring to FIG. 4, when the median filter is applied to the high-density material image, it can be observed that the white spots present between the spinal bones were significantly removed.

When a region in which a segmentation error has occurred is still present in the high-density material image, a region causing a segmentation error remains in a corrected image to hinder correction even though the correction process is iterated several times. However, according to this embodiment, when the separation unit 142 separates the high-density material image and then applies the median filter to the high-density material image, the segmentation error is removed, and thus it is possible to acquire a clearer image with no segmentation error as the correction process is iterated a larger number of times.

The scalar removal unit 145 generates a high-density conversion object by subtracting the scalar value computed by the scalar calculation unit 144 from the high-density material image to which the median filter is applied.

The scalar calculation unit 144 calculates a scalar value $\mu_{\tau(i)}$ using Equation 1:

$$\mu_{\tau(i)} = \frac{1}{N} \sum_{n=1}^{N} f_{tissue,\tau(i)}(n). \qquad \text{[Equation 1]}$$

Here, $f_{tissue,\tau(i)}$ is a low-density material image, and N is the number of low-density material elements. Also, i is the operating order of the correction process. That is, i is equal to one (i=1) when the correction process is performed for the first time, two (i=2) when the correction process is performed for the second time (one iteration), and three (i=3) when the correction process is performed for the third time (two iterations).

The reproduction unit 146 uses a forward projection method and an FDK image restoration algorithm when the high-density conversion is generated.

The correction process is iteratively performed by the computation unit 140 until the mean square error (MSE) of a reproduced image converges to a certain value.

The MSE of the reproduced image is computed using Equation 2:

$$MSE\ f_{errors,\tau(i)} = \frac{1}{N}\sum_{k=1}^{N}(f_{\tau(i)}(k) - f_{fdk}(k))^2. \quad [\text{Equation 2}]$$

Here, i is the number of iterations, $f_{errors,\tau(i)}$ is a reproduced image, $f_{\tau(i)}$ is a corrected image, $f_{fdk}$ is a start image, and N is the number of pixels of an image.

A reproduced image generated by the reproduction unit 146 has an MSE that increases as the number of iterations of the correction process increases, and a reproduced image used to generate a final corrected image has the maximum MSE.

Accordingly, even in a real medical environment where there is no normal image to be compared, correction is performed such that a corrected image is closer to a normal image.

Even when the number of iterations of the correction process of the computation unit 140 is five or less, it is sufficiently possible to obtain a high-quality correction image. Meanwhile, an apparatus for correcting a cone-beam artifact in a CBCT image according to another embodiment may be implemented by being included in a CBCT apparatus.

A method of correcting a cone-beam artifact in a CBCT image according to an embodiment of the present invention will be described below.

Figure 5:
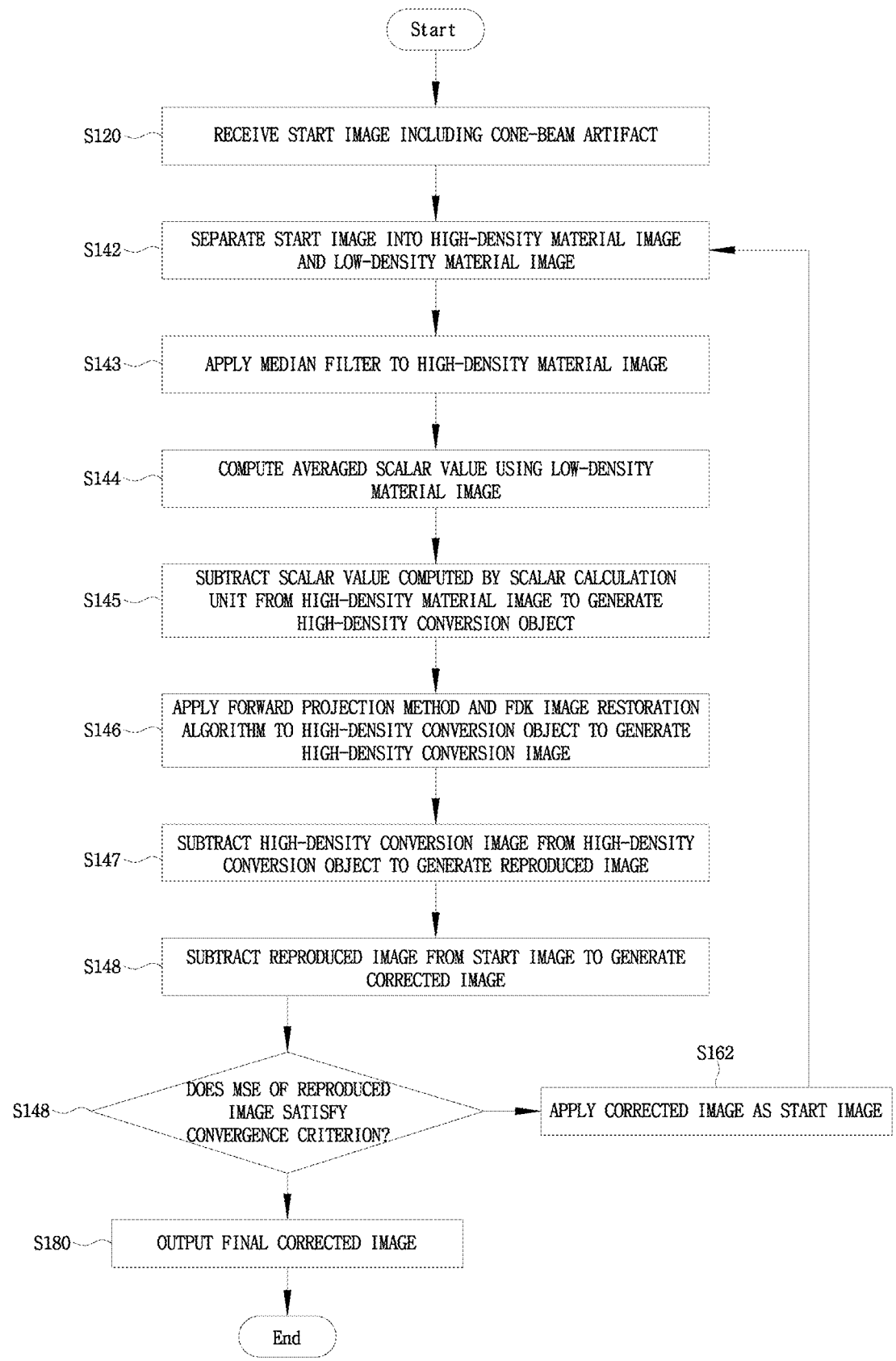
FIGS. 5 and 6 are flowcharts showing an operational sequence of a method of correcting a cone-beam artifact in a cone-beam computed tomography (CT) image according to an embodiment of the present invention.
Figure 6:
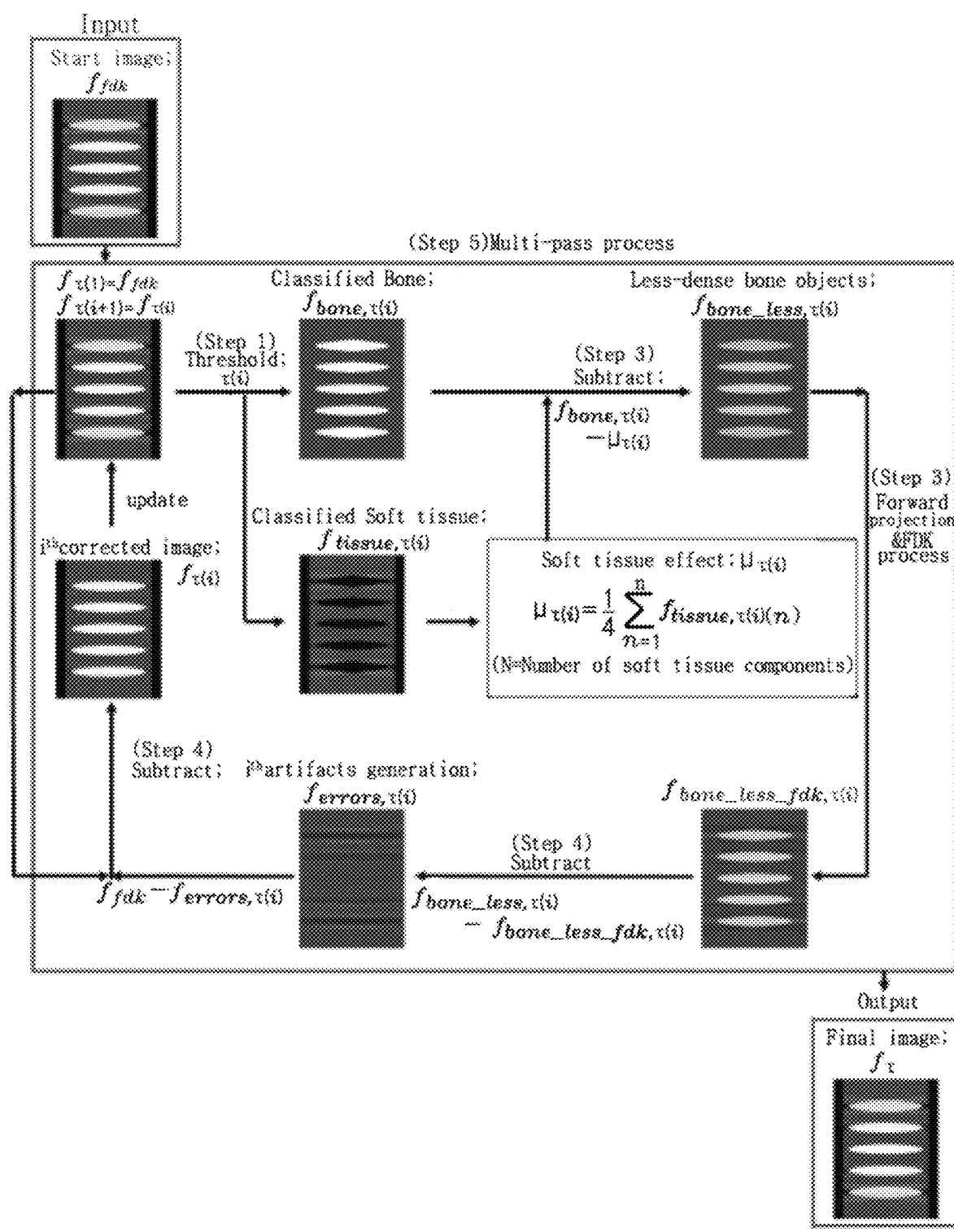

Referring to FIGS. 5 and 6, the method according to this embodiment includes an input unit 120 receiving a start image $f_{fdk}$ including a cone-beam artifact (S120), a separation unit 142 separating a high-density material image $f_{bone,\tau(i)}$ and a low-density material image $f_{tissue,\tau(i)}$ from the start image $f_{fdk}$ (S142), a scalar calculation unit 144 computing an averaged scalar value $\mu_{\tau(i)}$ using the low-density material image $f_{tissue,\tau(i)}$ generated by the separation unit 142 (S144), a scalar removal unit 145 subtracting the scalar value $\mu_{\tau(i)}$ computed by the scalar calculation unit 144 from the high-density material image $f_{bone,\tau(i)}$ generated by the separation unit 142 to generate a high-density conversion object $f_{bone\_less,\tau(i)}$ (S145), a reproduction unit 146 generating a high-density conversion image $f_{bone\_less\_fdk,\tau(i)}$ using the high-density conversion object $f_{bone\_less,\tau(i)}$ generated by the scalar removal unit 145 (S146), the reproduction unit 146 subtracting the high-density conversion image $f_{bone\_less\_fdk,\tau(i)}$ from the high-density conversion object $f_{bone\_less,\tau(i)}$ to generate a reproduced image $f_{errors,\tau(i)}$ (S147), a correction unit 148 generating a corrected image $f_{\tau(i)}$ by subtracting the reproduced image $f_{errors,\tau(i)}$ from the start image $f_{fdk}$ (S148), and an output unit 180 outputting a final corrected image $f_{\tau(i)}$ (S180).

The method further includes, after operation S148, a correction unit 148 computing an MSE value of the reproduced image and checking whether the MSE value satisfies a preset convergence criterion (S160) and the correction unit 148 applying the corrected image as a start image when the MSE value does not satisfy the preset criterion (S162).

Operations S142 to S148 are iterated until an MSE value of a corrected image satisfies a preset criterion.

In operation S142, a thresholding method is used to separate the start image into the high-density material image and the low-density material image.

In operation S142, the average of voxels corresponding to 90% or more of the maximum voxel of the high-density material region is computed, and a value corresponding to 55% to 75% of the average of the voxel is set as an initial threshold value for the thresholding method.

Each time the generation of the corrected image is iterated, the threshold value of the thresholding method is increased.

The threshold value may be linearly increased. For example, the threshold value may be increased by 2.5% to 5%.

In particular, when the number of iterations of generation of the corrected image exceeds three, the threshold value is no longer increased in order to prevent oversegmentation.

After operation S142, the method further includes the separation unit 142 applying a median filter to the separated high-density material image (S143).

In operation S144, the scalar value $\mu_{\tau(i)}$ is calculated using Equation 1.

In operation S146, the high-density conversion image is generated using a forward projection method and an FDK image restoration algorithm.

Experiment

Figure 7:
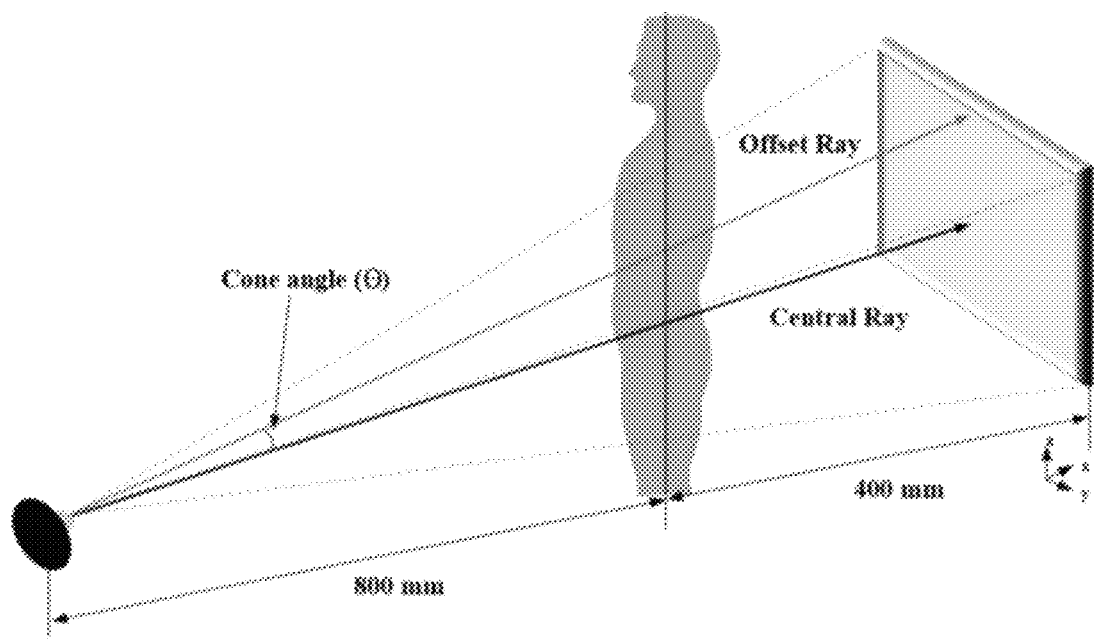
FIG. 7 is a schematic diagram showing a cone-beam CT system geometry configured for an experiment.

Referring to FIG. 7, a CBCT system geometry as shown in FIG. 7 was configured for this experiment. MATLAB R2017b was used as a simulator.

A first phantom (Defrise phantom) in which five oval slabs (corresponding to bones) with an X-ray attenuation coefficient of 0.4 cm$^{-1}$ are inserted into a cylinder (corresponding to soft tissue) with an X-ray attenuation coefficient of 0.18 cm$^{-1}$ was used as an object for verifying an embodiment of the present invention in order to generate a cone-beam artifact, which is generated according to the degree of offset in the z-axis from the center of an imaging member, well.

In addition, for a more realistic and complex anatomical structure, a second phantom (XCAT phantom) obtained by modeling a human chest was utilized in an energy band of 60 keV.

Each of the first phantom and the second phantom was configured in a 480×480×540 matrix. The size of the voxel was 0.517×0.517×0.517 mm$^3$, and 2×2×2 sub-voxels were allocated to one voxel in order to prevent a discretization error.

A projected image was acquired using a 3D forward projector which is developed by Gao.

Also, uniform noise with 10,000 photons per pixel was added to an image.

System parameters used for simulation are shown in Table 1, and this embodiment of the present invention was applied to a system with a cone angle of ±11.5 degrees.

TABLE 1

| Phantom | Defrise, XCAT |
| --- | --- |
| Source to iso-center distance | 800 mm |
| Detector to iso-center distance | 400 mm |
| Number of views | 720 |
| Number of incident X-ray photons per detector cell | 10,000 |
| Reconstruction algorithm | FDK |
| Detector cell size | 0.776 mm × 0.776 mm |
| Detector array size | 768 (row) × 512 (column) |
| Cone angle | ±11.5° |
| Reconstructed matrix size | 480 × 480 × 540 |
| Reconstructed volume size | 248 × 248 × 279 mm$^3$ |
| Reconstructed voxel size | 0.517 × 0.517 × 0.517 mm$^3$ |

Figure 8:
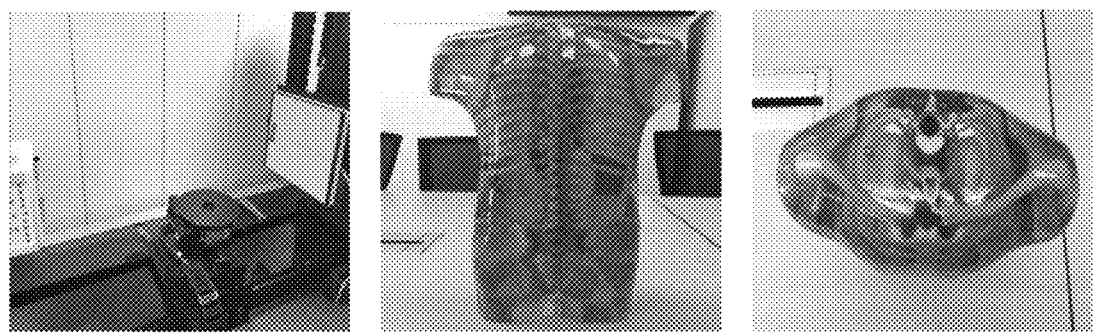
FIG. 8 is a diagram showing an environment used to image a pediatric phantom (on a left side), the rear surface of the pediatric phantom (on a middle side), and the top surface of the pediatric phantom (on a right side)

Also, this embodiment of the present invention was verified for a bench-top CT system with a cone angle of ±7.5 degrees using a pediatric phantom (referring to FIG. 8). Detailed parameters are shown in Table 2.

TABLE 2

| Phantom | Pediatric |
|---|---|
| Source to iso-center distance | 800 mm |
| Detector to iso-center distance | 400 mm |
| Focal spot size of X-ray source | 0.6 × 0.6 mm$^2$ |
| X-ray source operating mode | 90 kVp, 8 mA |
| Number of views | 720 |
| Detector cell size | 0.776 mm × 0.776 mm |
| Detector array size | 384 (row) × 512 (column) |
| Cone angle | ±7.5° |
| Reconstructed matrix size | 480 × 480 × 343 |
| Reconstructed volume size | 248 × 248 × 178 mm$^3$ |
| Reconstructed voxel size | 0.517 × 0.517 × 0.517 mm$^3$ |

In this experiment, the first phantom, the second phantom, and the pediatric phantom were used to compare this embodiment of the present invention to results of the two-pass algorithm and total-variation minimization-based iterative reconstruction (TV-IR).

For the two-pass algorithm, a final corrected image was acquired by setting a threshold value for high-density material estimation to be equal to 0.26 cm$^{-1}$ for the first phantom, 0.27 cm$^{-1}$ for the second phantom, and 0.26 cm$^{-1}$ for the pediatric phantom.

Figure 9:
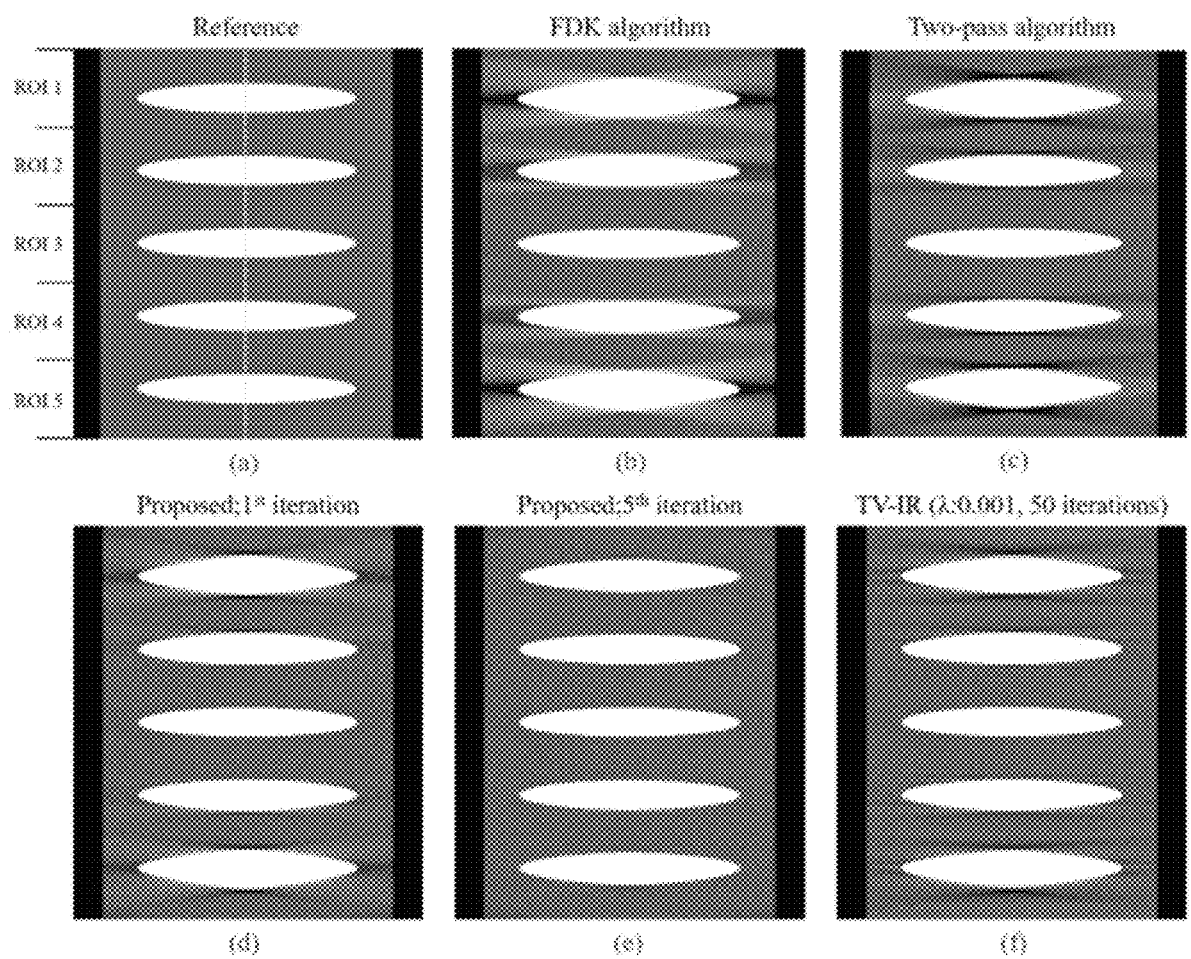
FIG. 9 is a diagram showing, for a first phantom (Defrise phantom), (a) a basic image, (b) an image obtained through conversion using the FDK algorithm, (c) an image obtained through correction using the two-pass algorithm, (d) an image obtained through correction in one iteration of an embodiment of the present invention, (e) an image obtained through correction in five iterations of an embodiment of the present invention, and (f) an image obtained through correction using TV-IR.
Figure 10:
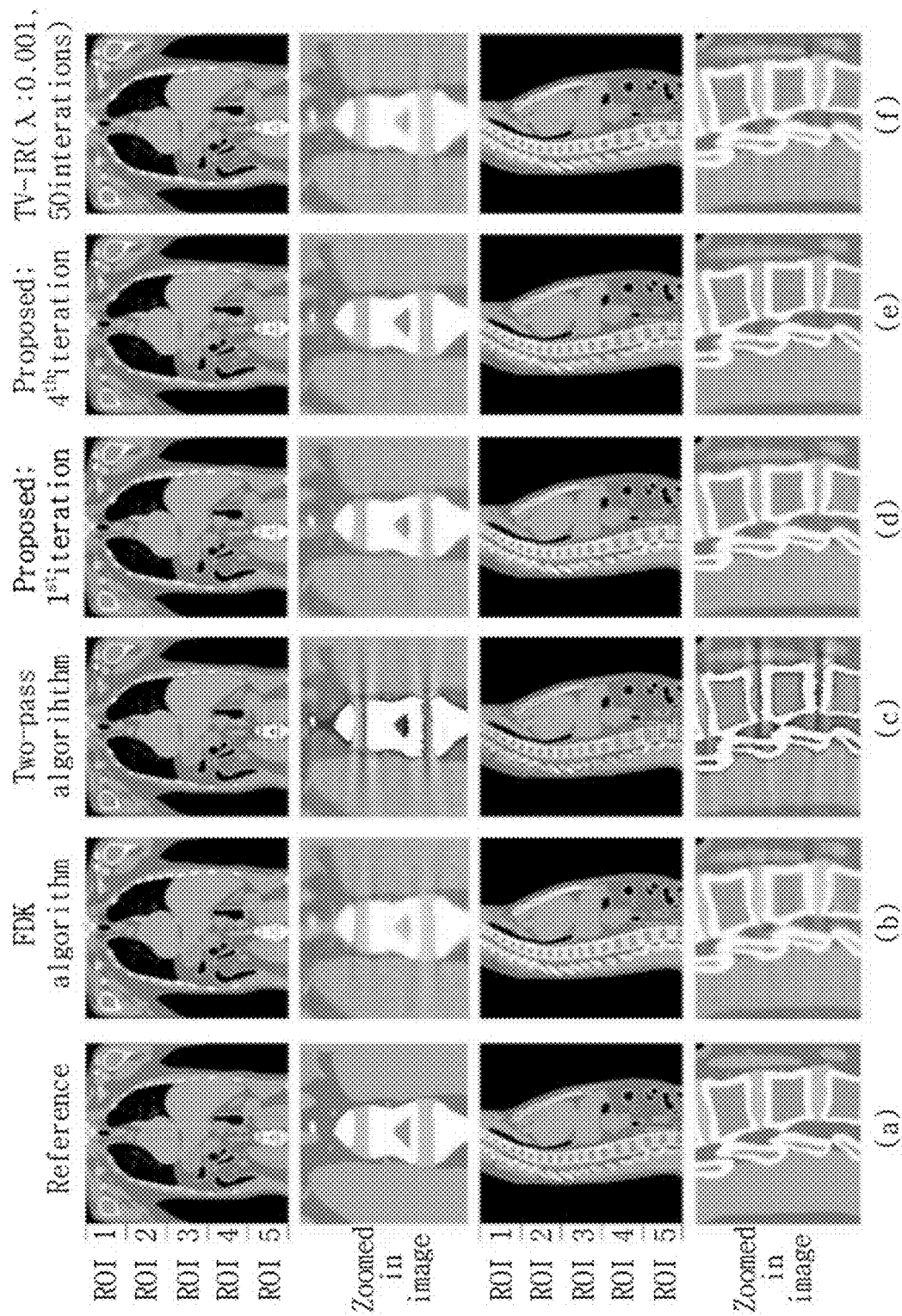
FIG. 10 is a diagram showing, for a second phantom (XCAT phantom), (a) a basic image, (b) an image obtained through conversion using the FDK algorithm, (c) an image obtained through correction using the two-pass algorithm, (d) an image obtained through correction in one iteration of an embodiment of the present invention, (e) an image obtained through correction in four iterations of an embodiment of the present invention, and (f) an image obtained through correction using TV-IR.
Figure 11:
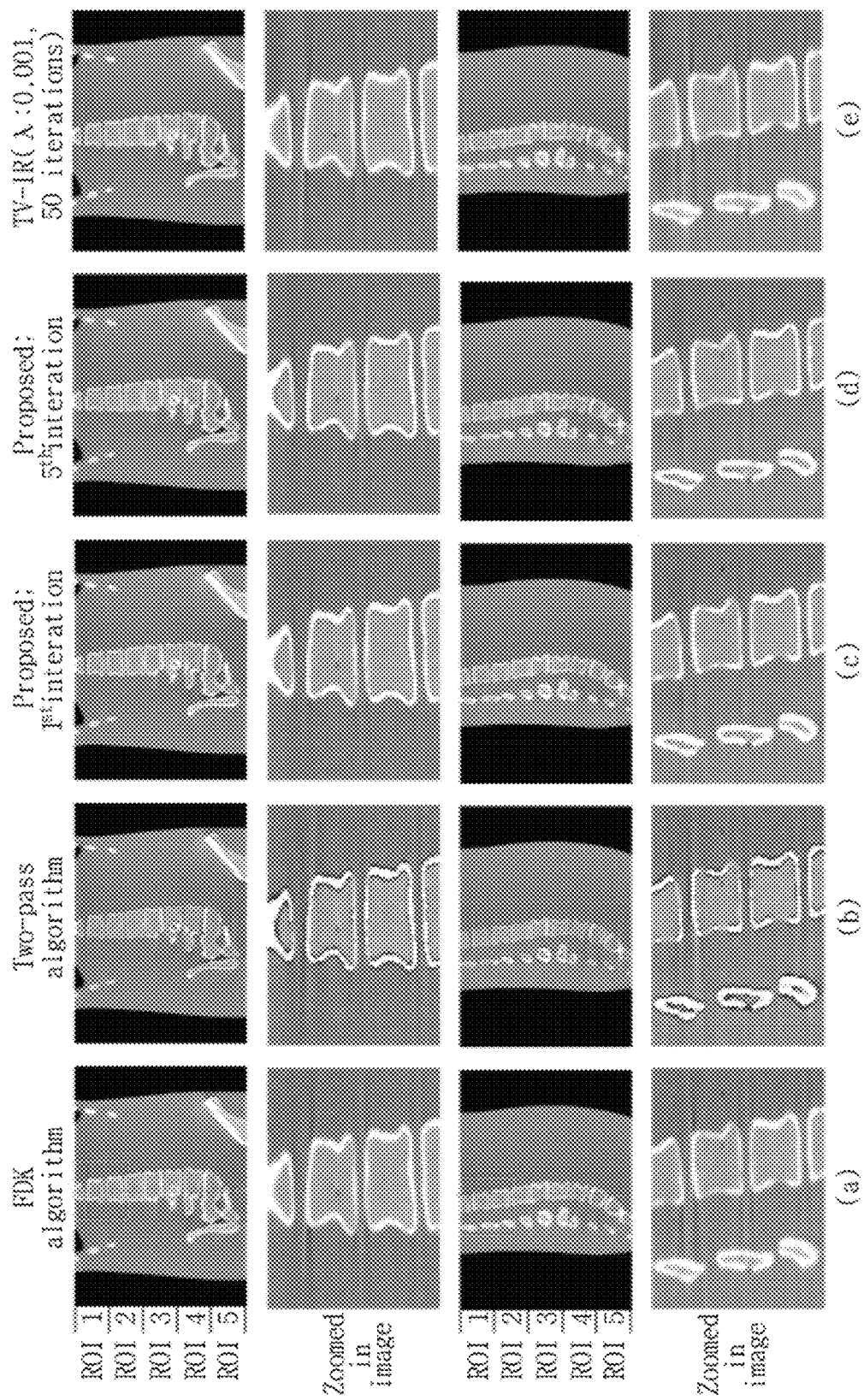
FIG. 11 is a diagram showing, for a pediatric phantom, (a) an image obtained through conversion using the FDK algorithm, (b) an image obtained through correction using the two-pass algorithm, (c) an image obtained through correction in one iteration of an embodiment of the present invention, (d) an image obtained through correction in five iterations of an embodiment of the present invention, and (e) an image obtained through correction using TV-IR.

FIG. 9 shows an image of the first phantom (Defrise phantom), FIG. 10 shows an image of the second phantom (XCAT phantom), and FIG. 11 shows an image of the pediatric phantom.

Referring to FIGS. 9C, 10C, and 11B, the conventional two-pass algorithm is greatly affected by a cone-beam artifact in the case of a bone object having a large offset in the z-axis where a cone-beam angle is large. In particular, since the two-pass algorithm does not consider a cone-beam artifact generated in the soft tissue, a severe distortion occurs compared to a reference image. Also, in the case of high-density portions of regions ROI 1 and ROI 5, it was found that a boundary was unstable due to the inability to handle a segmentation error.

Meanwhile, in order to perform correction performance comparison according to the number of iterations of this embodiment of the present invention, corrected images obtained by performing one iteration and corrected images obtained by performing iterations until the MSE converges were prepared for the three phantoms.

Referring to FIGS. 9D, 10D, and 11C, the same threshold value as that of the two-pass algorithm was applied while this embodiment of the present invention was being iterated once. Even though this embodiment of the present invention was iterated only once, it was confirmed that a segmentation error for bones was reduced by a 3D median filter and a better image could be acquired by considering soft tissue compared to the conventional two-pass algorithm.

Also, referring to FIGS. 9E, 10E, and 11D, when this embodiment of the present invention was iterated until the MSE converges, the threshold value of the first phantom was increased in the order of 0.26 cm$^{-1}$, 0.27 cm$^{-1}$, and 0.28 cm$^{-1}$ each time the correction process was iterated. Then, the threshold value was fixed to the last value in the fourth-order. The threshold value of the second phantom was increased in the order of 0.27 cm$^{-1}$, 0.28 cm$^{-1}$, and 0.29 cm$^{-1}$ each time the correction process is iterated, and then was fixed to the last value in the fourth-order. The threshold value of the pediatric phantom was increased in the order of 0.26 cm$^{-1}$, 0.27 cm$^{-1}$, and 0.28 cm$^{-1}$ each time the correction process is iterated and then was fixed to the last value in the fourth-order.

Figure 12:
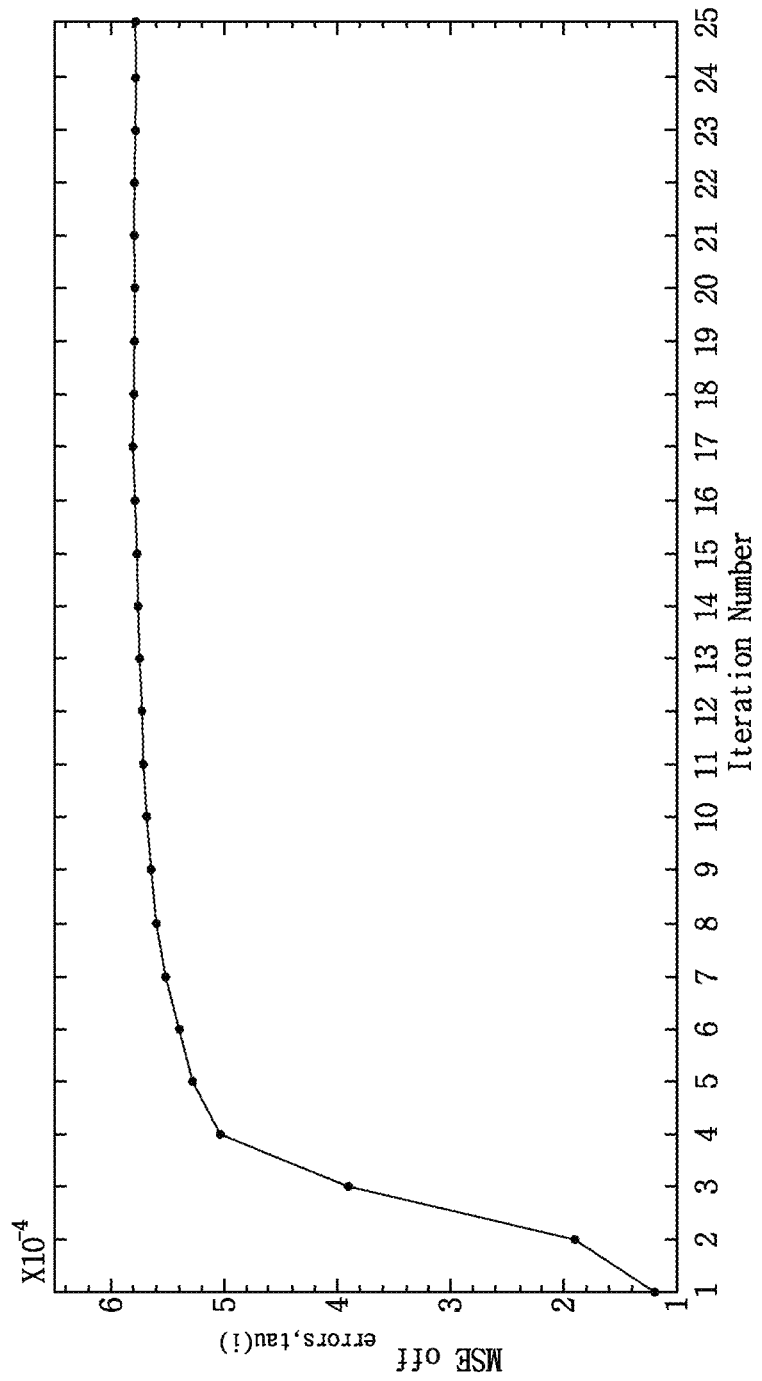
FIG. 12 is a convergence graph of an embodiment of the present at the first phantom.

FIG. 12 is a convergence graph of an embodiment of the present invention at the first phantom. According to an embodiment of the present invention, the MSE increased as the corrected image becomes closer to the reference image.

Table 3 is an MSE result for the first phantom.

TABLE 3

| ROI | FDK | Two-pass | Proposed; 1st | Proposed; 5th | TV-IR |
|---|---|---|---|---|---|
| 1 | 20.00 × 10$^{-4}$ | 16.00 × 10$^{-4}$ | 10.00 × 10$^{-4}$ | 2.77 × 10$^{-4}$ | 6.18 × 10$^{-4}$ |
| 2 | 5.56 × 10$^{-4}$ | 5.07 × 10$^{-4}$ | 2.38 × 10$^{-4}$ | 0.70 × 10$^{-4}$ | 1.99 × 10$^{-4}$ |
| 3 | 0.61 × 10$^{-4}$ | 0.60 × 10$^{-4}$ | 0.48 × 10$^{-4}$ | 0.48 × 10$^{-4}$ | 0.48 × 10$^{-4}$ |
| 4 | 5.55 × 10$^{-4}$ | 5.04 × 10$^{-4}$ | 2.37 × 10$^{-4}$ | 0.70 × 10$^{-4}$ | 1.98 × 10$^{-4}$ |
| 5 | 20.00 × 10$^{-4}$ | 16.00 × 10$^{-4}$ | 10.00 × 10$^{-4}$ | 2.79 × 10$^{-4}$ | 6.19 × 10$^{-4}$ |

Table 4 shows a structural similarity index (SSIM) result for the first phantom.

TABLE 4

| ROI | FDK | Two-pass | Proposed; 1st | Proposed; 5th | TV-IR |
|---|---|---|---|---|---|
| 1 | 0.9256 | 0.9522 | 0.9662 | 0.9912 | 0.9802 |
| 2 | 0.9784 | 0.9846 | 0.9924 | 0.9978 | 0.9937 |
| 3 | 0.9949 | 0.9978 | 0.9985 | 0.9985 | 0.9985 |
| 4 | 0.9787 | 0.9847 | 0.9924 | 0.9978 | 0.9937 |
| 5 | 0.9257 | 0.9518 | 0.9660 | 0.9911 | 0.9801 |

Figure 13:
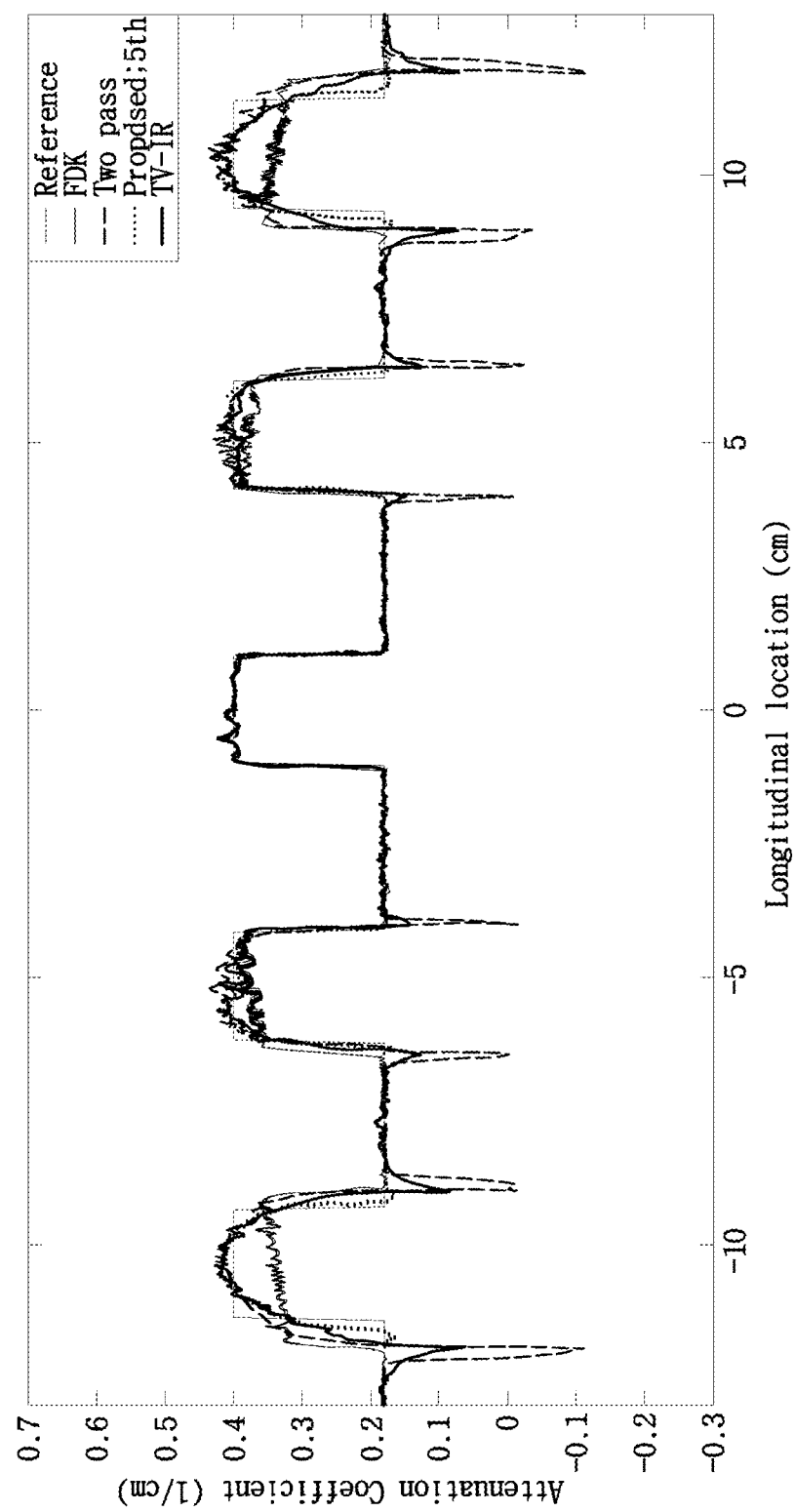
FIG. 13 is a graph showing the vertical profile of the first phantom.

FIG. 13 is a graph showing the vertical profile of the first phantom.

Figure 14:
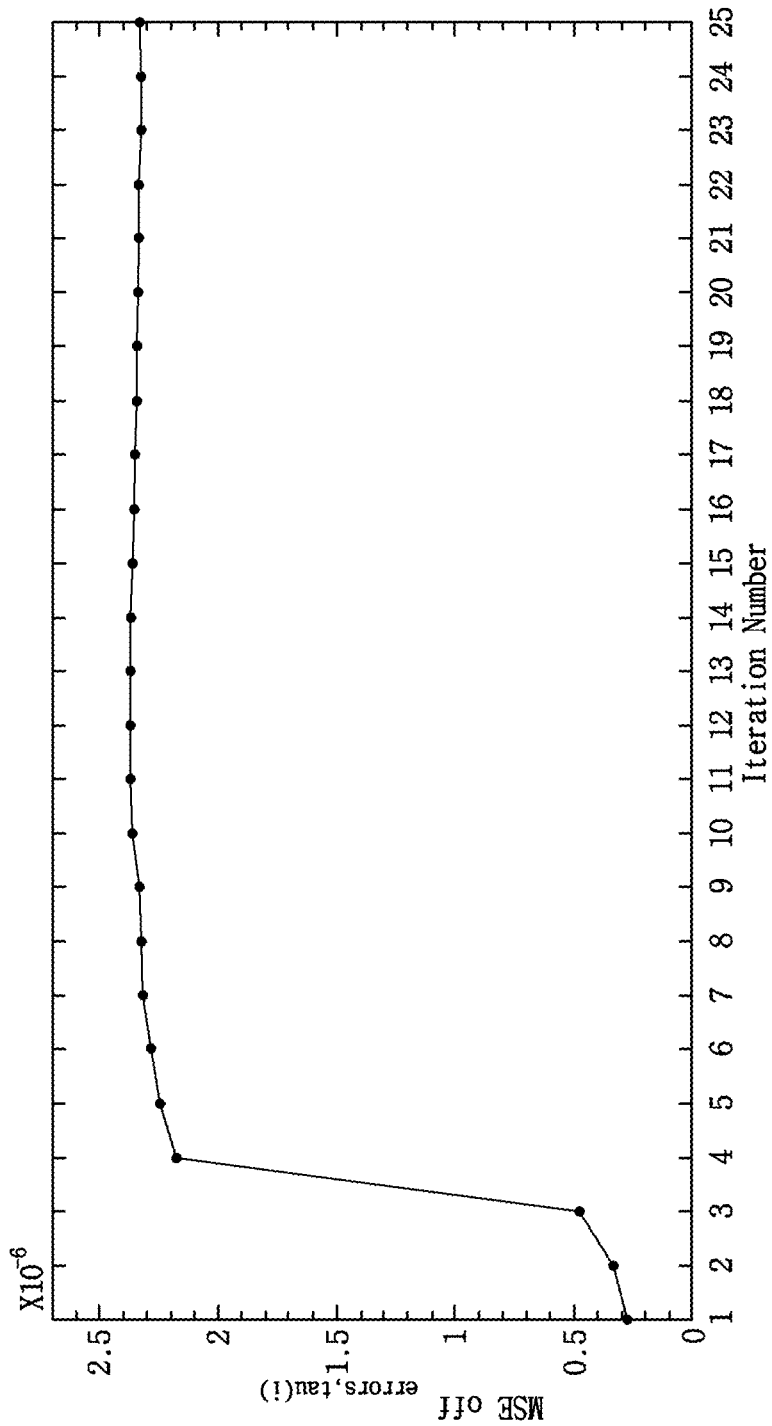
FIG. 14 is a convergence graph of an embodiment of the present invention at the second phantom.

FIG. 14 is a convergence graph of an embodiment of the present invention at the second phantom.

Table 5 is an MSE result for the second phantom.

TABLE 5

| | Coronal (×10$^{-4}$) | | | | | Sagittal (×10$^{-4}$) | | | | |
|---|---|---|---|---|---|---|---|---|---|---|
| ROI | FDK | Two-pass | Proposed; 1st | Proposed; 4th | TV-IR | FDK | Two-pass | Proposed; 1st | Proposed; 4th | TV-IR |
| 1 | 1.15 | 2.17 | 0.68 | 0.52 | 0.61 | 1.56 | 3.73 | 1.30 | 1.07 | 1.26 |
| 2 | 1.83 | 2.35 | 1.56 | 1.20 | 1.33 | 1.14 | 3.67 | 0.63 | 0.62 | 0.54 |
| 3 | 2.14 | 2.97 | 1.72 | 1.68 | 1.69 | 1.59 | 3.74 | 1.35 | 1.14 | 1.34 |

TABLE 5-continued

| | | Coronal (×10$^{-4}$) | | | | | Sagittal (×10$^{-4}$) | | | |
|---|---|---|---|---|---|---|---|---|---|---|
| ROI | FDK | Two-pass | Proposed; 1st | Proposed; 4th | TV-IR | FDK | Two-pass | Proposed; 1st | Proposed; 4th | TV-IR |
| 4 | 2.74 | 3.63 | 1.89 | 1.59 | 1.75 | 2.10 | 4.03 | 1.08 | 0.96 | 1.04 |
| 5 | 4.75 | 6.65 | 2.98 | 1.93 | 2.96 | 1.93 | 4.06 | 1.32 | 1.21 | 1.28 |

Table 6 is an SSIM result for the second phantom.

TABLE 6

| | | Coronal | | | | | Sagittal | | | |
|---|---|---|---|---|---|---|---|---|---|---|
| ROI | FDK | Two-pass | Proposed; 1st | Proposed; 4th | TV-IR | FDK | Two-pass | Proposed; 1st | Proposed; 4th | TV-IR |
| 1 | 0.9961 | 0.9914 | 0.9969 | 0.9973 | 0.9970 | 0.9952 | 0.9872 | 0.9951 | 0.9965 | 0.9952 |
| 2 | 0.9919 | 0.9899 | 0.9931 | 0.9969 | 0.9954 | 0.9961 | 0.9871 | 0.9955 | 0.9967 | 0.9958 |
| 3 | 0.9910 | 0.9876 | 0.9919 | 0.9932 | 0.9932 | 0.9950 | 0.9893 | 0.9961 | 0.9961 | 0.9961 |
| 4 | 0.9830 | 0.9767 | 0.9863 | 0.9936 | 0.9930 | 0.9941 | 0.9898 | 0.9965 | 0.9967 | 0.9963 |
| 5 | 0.9713 | 0.9635 | 0.9850 | 0.9965 | 0.9945 | 0.9937 | 0.9869 | 0.9958 | 0.9960 | 0.9956 |

Figure 15:
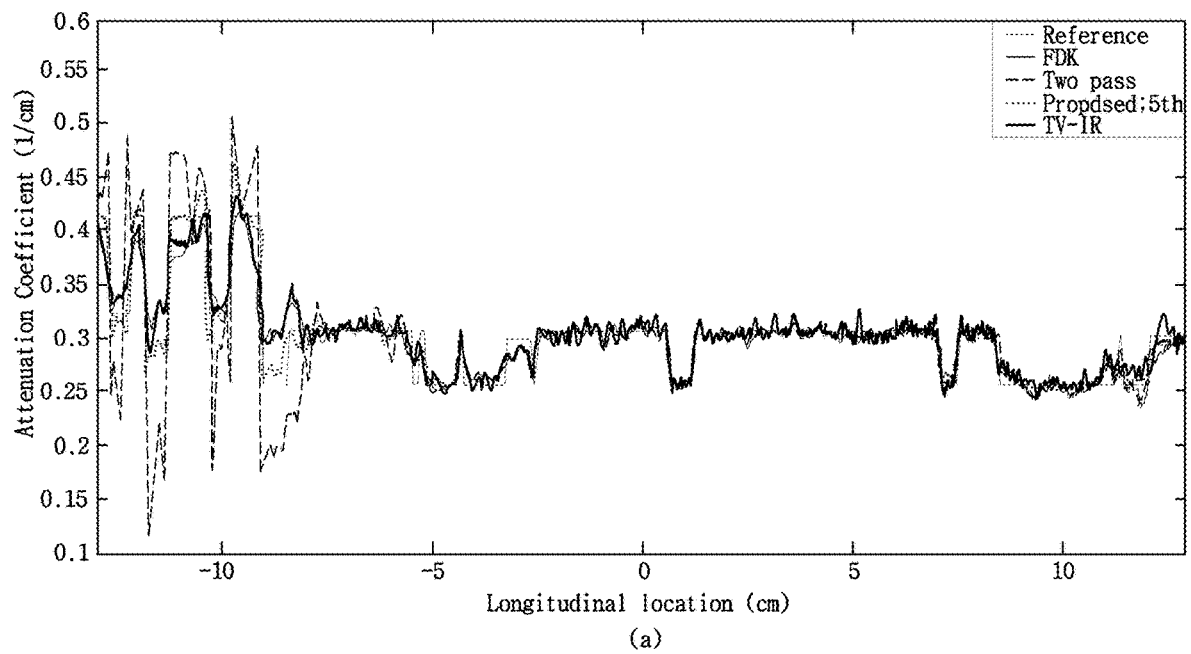
FIG. 15 is a graph showing the vertical profile of the second phantom wherein (a) indicates coronal and (b) indicates sagittal slices.
Figure 15:
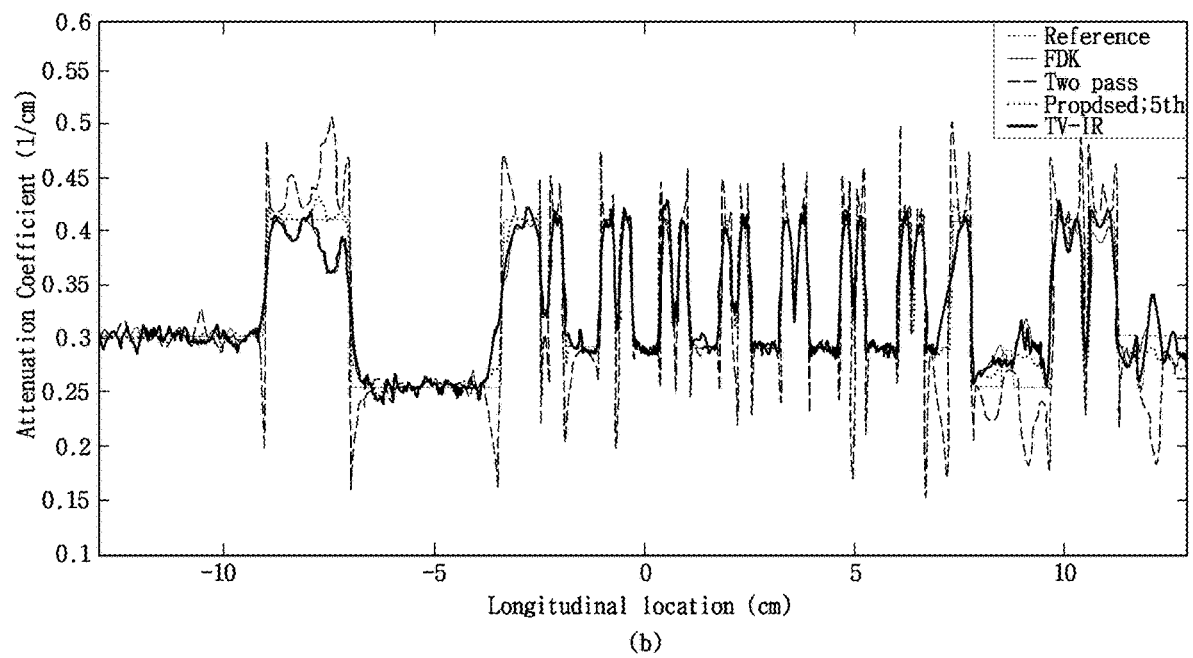

FIG. 15 is a graph showing the vertical profile of the second phantom wherein (a) indicates coronal and (b) indicates sagittal slices.

Figure 16:
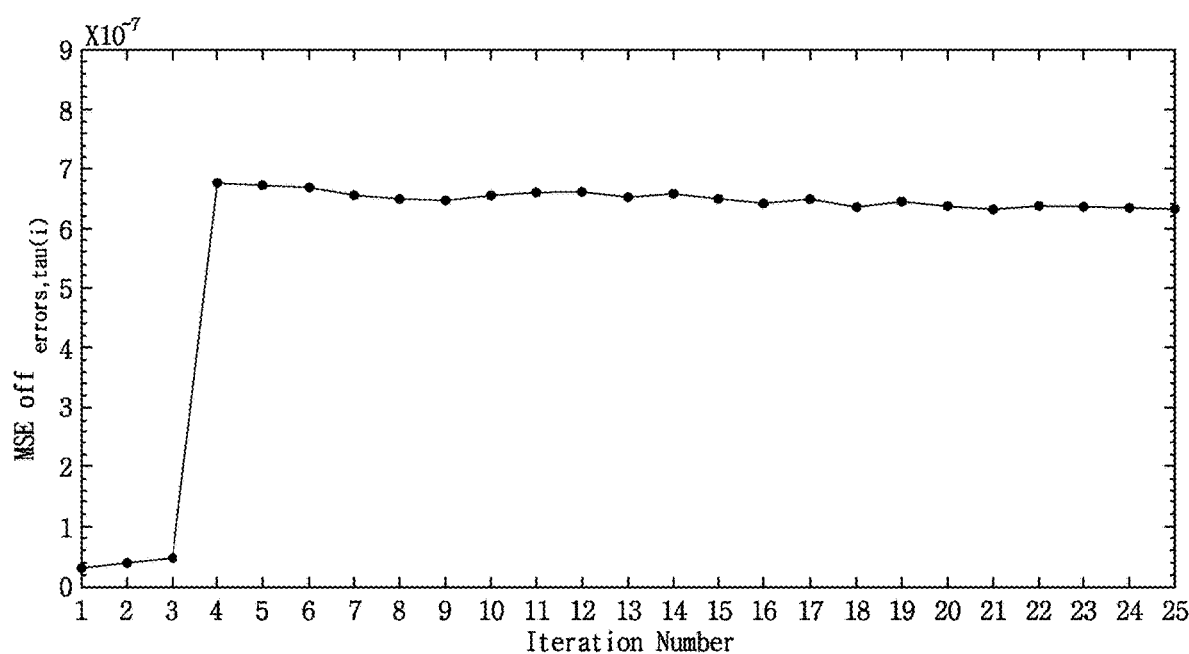
FIG. 16 is a convergence graph of an embodiment of the present invention at the pediatric phantom.

FIG. 16 is a convergence graph of an embodiment of the present invention in terms of the pediatric phantom.

Figure 17:
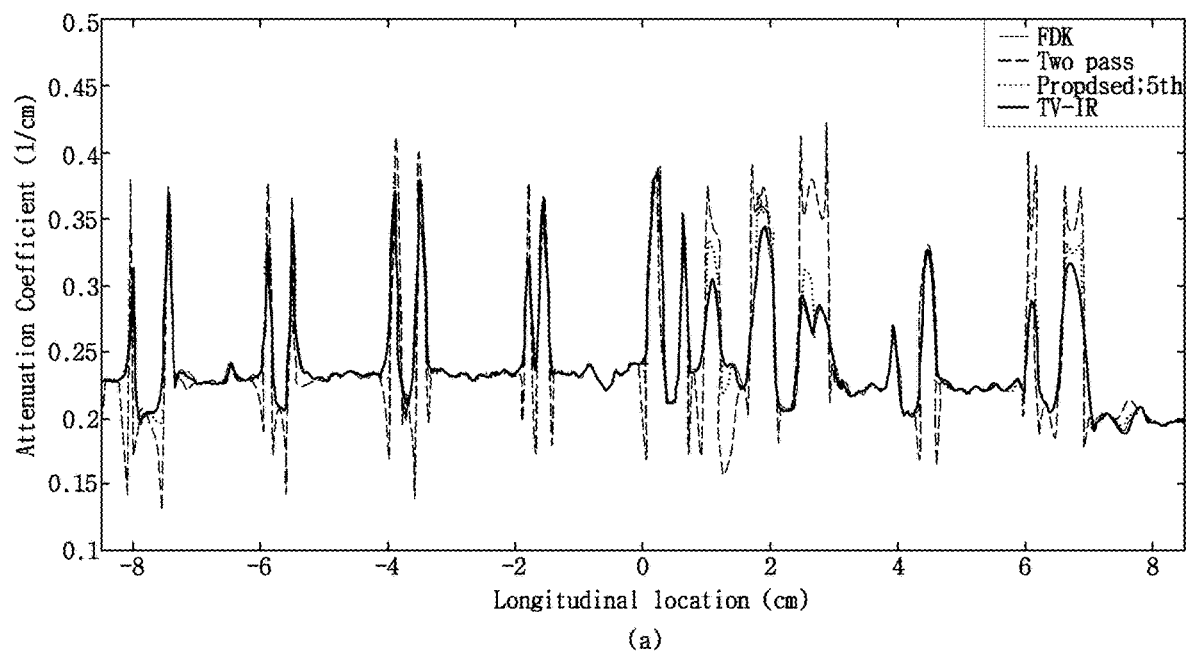
FIG. 17 is a graph showing the vertical profile of the pediatric phantom wherein (a) indicates coronal and (b) indicates sagittal slices.
Figure 17:
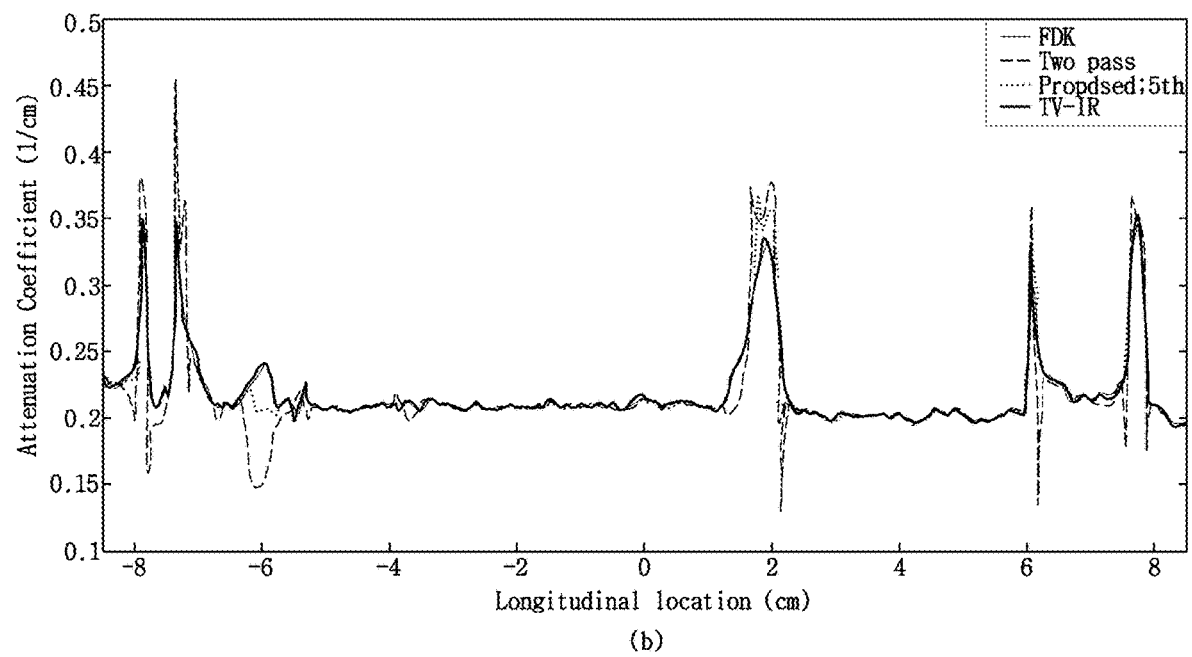

FIG. 17 is a graph showing the vertical profile of the pediatric phantom wherein (a) indicates coronal and (b) indicates sagittal slices.

In order to compare an embodiment of the present invention to the conventional technique, quantitative comparison using the MSE and SSIM values and qualitative comparison using the resulting image and the vertical profile were performed.

The MSE is computed using Equation 2. Also, the SSIM is computed using Equation 3:

$$SSIM(A, B) = \frac{(2\mu_A \mu_B + C_1)(2\sigma_{AB} + C_2)}{(\mu_A^2 + \mu_B^2 + C_1)(\sigma_A^2 + \sigma_B^2 + C_2)}.$$ [Equation 3]

Here, $\mu_A$ is the average intensity of corrected image A, and $\sigma_A$ is the standard deviation of corrected image A. $\mu_B$ is the average intensity of corrected image B, and $\sigma_B$ is the standard deviation of corrected image B. $\sigma_{AB}$ is a covariance between corrected images A and B. $C_1$ and $C_2$ are coefficients for SSIM calculation, and values of 0 to 1 were applied as the coefficients. In this experiment, $C_1 = 6.5 \times 10^{-4}$ and $C_2 = 2.6 \times 10^{-4}$ were applied.

As a result of the comparison, it was confirmed that cone-beam artifact correction performance was best when this embodiment of the present invention was iterated until the MSE converges.

Also, when this embodiment of the present invention is iterated until the MSE converges, the number of iterations is just four or five. Thus, under the experimental system specification ((NVIDIA Tesla S2050), corrected images could be obtained in less than three minutes.

Also, an ROI in an image was segmented into five sections according to the cone angle. As a result of the comparison of the reference image, the initial cone-beam artifact occurrence image, the conventional algorithm, and the RMSE result and the vertical intensity profile result of an embodiment of the present invention, it could be confirmed that for all of the three phantoms, the present invention exhibits more excellent cone-beam artifact correction performance than the conventional two-pass algorithm.

Referring to FIGS. 9F, 10F, and 11E, images were also corrected using the TV-IR algorithm. For all the phantoms, a regular parameter λ was set to 0.001, and the correction process was iterated 50 times.

When comparing the cone-beam artifact correction result of the TV-IR algorithm to an embodiment of the present invention, it was shown that this embodiment of the present invention, which is iterated until the MSE converges, has a better image result compared to the number of iterations than the TV-IR. This proves that the embodiment of the present invention is superior to the conventional TV-IR algorithm when actually applied to a real-time system.

Although exemplary embodiments of the present invention have been described above, various changes, modifications, and equivalents of the present invention can be made. It is apparent that the above embodiments of the present invention may be appropriately modified and then equally applied. Therefore, the above description is not intended to limit the scope of the present invention as defined by the following claims.

The invention claimed is:

1. An apparatus for correcting a cone-beam artifact in a cone-beam computed tomography image, the apparatus comprising:
   an input unit configured to receive a start image including a cone-beam artifact;
   a computation unit configured to separate a high-density material image and a low-density material image from the start image received by the input unit, generate a reproduced image in which the cone-beam artifact is reproduced using the low-density material image, execute a correction process for subtracting the reproduced image from the start image to generate a corrected image, and iterate the correction process using the corrected image as a start image; and
   an output unit configured to output a final corrected image generated by the computation unit.

2. The apparatus of claim 1, wherein the correction process of the computation unit is iterated until a mean squared error (MSE) of the reproduced image satisfies a preset convergence criterion.

3. The apparatus of claim 2, wherein the number of iterations of the correction process of the computation unit is five or less.

4. The apparatus of claim 1, wherein the computation unit comprises:
a separation unit configured to separate the high-density material image and the low-density material image from the start image;
a scalar calculation unit configured to compute an averaged scalar value using the low-density material image generated by the separation unit;
a scalar removal unit configured to subtract the scalar value computed by the scalar calculation unit from the high-density material image generated by the separation unit to generate a high-density conversion object;
a reproduction unit configured to generate a high-density conversion image using the high-density conversion object generated by the scalar removal unit and generate a reproduced image by subtracting the high-density conversion image from the high-density conversion object; and
a correction unit configured to generate a corrected image by subtracting the reproduced image from the start image.

5. The apparatus of claim 4, wherein the separation unit uses a thresholding method to separate the start image into the high-density material image and the low-density material image.

6. The apparatus of claim 5, wherein the separation unit computes an average of voxels corresponding to 90% or more of the maximum voxel in a high-density material region and sets a value corresponding to 55% to 75% of the average of the voxel as an initial threshold value for the thresholding method.

7. The apparatus of claim 6, wherein the separation unit increases the threshold value for the thresholding method each time the correction process is iterated.

8. The apparatus of claim 7, wherein the threshold value is linearly increased each time the correction process is iterated.

9. The apparatus of claim 8, wherein the threshold value is increased by 2.5% to 5%.

10. The apparatus of claim 8, wherein the threshold value is no longer increased to prevent oversegmentation when the number of iterations of the correction process exceeds three.

11. The apparatus of claim 4, wherein the separation unit applies a median filter to the separated high-density material image.

12. The apparatus of claim 4, wherein the scalar calculation unit calculates the scalar value ($\mu_{\tau(1)}$) using the following equation:

$$\mu_{\tau(1)} = \frac{1}{N} \sum_{n=1}^{N} f_{tissue,\tau(1)}(n)$$

where $f_{tissue,\tau(i)}$ is a low-density material image, N is the number of low-density material elements, and i is an operating order of the correction process.

13. The apparatus of claim 4, wherein the reproduction unit generates the high-density conversion image using a forward projection method and a Feldkamp, Davis and Kress (FDK) algorithm.

14. A method of correcting a cone-beam artifact in a cone-beam computed tomography image, the method comprising:

causing an input unit to receive a start image including a cone-beam artifact;
causing a separation unit to separate a high-density material image and a low-density material image from the start image;
causing a scalar calculation unit to compute an averaged scalar value using the low-density material image generated by the separation unit;
causing a scalar removal unit to subtract the scalar value computed by the scalar calculation unit from the high-density material image generated by the separation unit to generate a high-density conversion object;
causing a reproduction unit to generate a high-density conversion image using the high-density conversion object generated by the scalar removal unit;
causing the reproduction unit to generate a reproduced image by subtracting the high-density conversion image from the high-density material image generated by the separation unit;
causing a correction unit to generate a corrected image by subtracting the reproduced image from the start image; and
causing an output unit to output a final corrected image.

15. The method of claim 14, further comprising, after the causing of the correction unit to generate the corrected image by subtracting the reproduced image from the start image:
causing the correction unit to compute a mean-squared error (MSE) of the reproduced image and check whether the MSE satisfies a preset convergence criterion; and
causing the correction unit to apply the corrected image as a start image when the MSE does not satisfy the preset convergence criterion,
wherein a process from the causing of the separation unit to separate the high-density material image and the low-density material image from the start image to the causing of the correction unit to generate a corrected image by subtracting the reproduced image from the start image is iterated until an MSE of the corrected image satisfies a preset criterion.

16. The method of claim 15, wherein the causing of the separation unit to separate the high-density material image and the low-density material image from the start image comprises separating the start image into the high-density material image and the low-density material image using a thresholding method.

17. The method of claim 16, wherein the causing of the separation unit to separate the high-density material image and the low-density material image from the start image comprises computing an average of voxels corresponding to 90% or more of the maximum voxel in a high-density material region and to set a value corresponding to 55% to 75% of the average of the voxel as an initial threshold value for the thresholding method.

18. The method of claim 17, wherein the causing of the separation unit to separate the high-density material image and the low-density material image from the start image comprises increasing the threshold value for the thresholding method each time the generation of the corrected image is iterated.

19. The method of claim 18, wherein the causing of the separation unit to separate the high-density material image and the low-density material image from the start image comprises increasing the threshold value linearly.

20. The method of claim 19, wherein the causing of the separation unit to separate the high-density material image and the low-density material image from the start image comprises increasing the threshold value by 2.5% to 5%.

21. The method of claim 19, wherein the causing of the separation unit to separate the high-density material image and the low-density material image from the start image comprises no longer increasing the threshold value in order to prevent oversegmentation when the number of generations of the corrected image exceeds three.

22. The method of claim 14, further comprising, after the causing of the separation unit to separate the high-density material image and the low-density material image from the start image, causing the separation unit to apply a median filter to the separated high-density material image.

23. The method of claim 14, wherein the causing of the scalar calculation unit to compute the averaged scalar value using the low-density material image generated by the separation unit comprises calculating the scalar value ($\mu_{\tau(1)}$) using the following equation:

$$\mu_{\tau(1)} = \frac{1}{N}\sum_{n=1}^{N} f_{tissue,\tau(1)}(n)$$

where $f_{tissue,\tau(i)}$ is a low-density material image, N is the number of low-density material elements, i is an operating order of the correction process.

24. The method of claim 14, wherein the causing of the reproduction unit to generate the high-density conversion image using the high-density conversion object generated by the scalar removal unit comprises generating the high-density conversion image using a forward projection method and a Feldkamp, Davis and Kress (FDK) algorithm.

25. A cone-beam computed tomography apparatus comprising:
an input unit configured to receive a start image including a cone-beam artifact;
a computation unit configured to separate a high-density material image and a low-density material image from the start image received by the input unit, generate a reproduced image in which the cone-beam artifact is reproduced using the low-density material image, execute a correction process for subtracting the reproduced image from the start image to generate a corrected image, and iterate the correction process using the corrected image as a start image; and
an output unit configured to output a final corrected image generated by the computation unit.

* * * * *